(12) United States Patent
Delisle et al.

(10) Patent No.: US 7,422,015 B2
(45) Date of Patent: Sep. 9, 2008

(54) ARRANGEMENT AND METHOD FOR DETECTING SPONTANEOUS RESPIRATORY EFFORT OF A PATIENT

(75) Inventors: Matt S. Delisle, Pewaukee, WI (US); Robert Q. Tham, Middleton, WI (US); Duncan P. L. Bathe, Fitchburg, WI (US)

(73) Assignee: The General Electric Company, Schenectady, NY (US)

( * ) Notice: Subject to any disclaimer, the term of this patent is extended or adjusted under 35 U.S.C. 154(b) by 394 days.

(21) Appl. No.: 11/285,121

(22) Filed: Nov. 22, 2005

(65) Prior Publication Data

US 2007/0113851 A1    May 24, 2007

(51) Int. Cl.
*A61M 16/00* (2006.01)
(52) U.S. Cl. ................................. 128/207.18
(58) Field of Classification Search ............ 128/207.18, 128/203.22, 204.18, 912, 204.23, 204.26, 128/206.11, 207.17
See application file for complete search history.

(56) References Cited

U.S. PATENT DOCUMENTS

| | | | | |
|---|---|---|---|---|
| 4,258,710 A | * | 3/1981 | Reber | 128/204.18 |
| 5,400,781 A | * | 3/1995 | Davenport | 128/206.28 |
| 5,474,060 A | * | 12/1995 | Evans | 128/204.22 |
| 6,659,101 B2 | * | 12/2003 | Berthon-Jones | 128/204.21 |
| 6,849,049 B2 | * | 2/2005 | Starr et al. | 600/538 |
| 7,305,988 B2 | * | 12/2007 | Acker et al. | 128/204.18 |
| 2002/0116994 A1 | * | 8/2002 | Heinonen | 73/196 |
| 2005/0011523 A1 | * | 1/2005 | Aylsworth et al. | 128/207.18 |

* cited by examiner

*Primary Examiner*—Steven O Douglas
(74) *Attorney, Agent, or Firm*—Andrus, Sceales, Starke & Sawall, LLP

(57) ABSTRACT

An arrangement and method for detecting spontaneous respiratory effort of a patient receiving ventilatory support via a breathing circuit. A patient/breathing circuit interface is adapted to provide a closed connection between a breathing passage of the patient and the breathing circuit. A sensor is disposed at least partially in the breathing passage of the patient and arranged to sense flow of gas through the breathing passage. The arrangement and method individually or in addition to the airway pressure measurement promotes reliable and rapid detection of breathing efforts of a non-intubated patient to promote efficient augmentation of patient breathing.

18 Claims, 3 Drawing Sheets

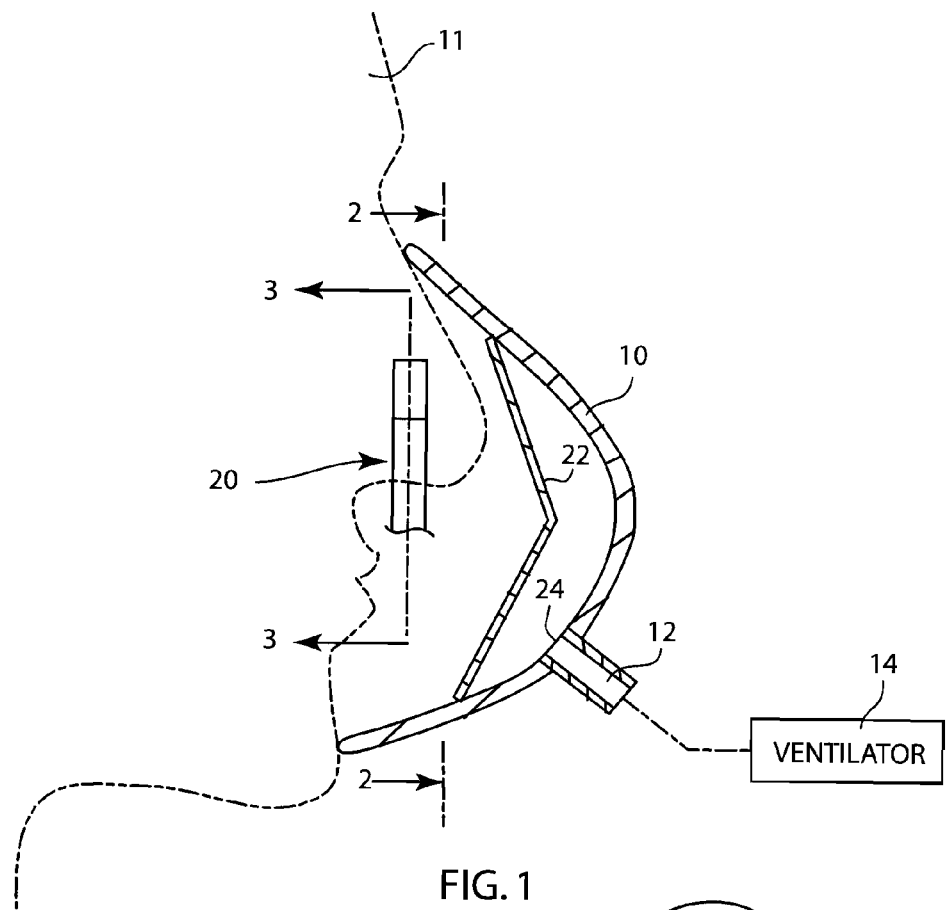
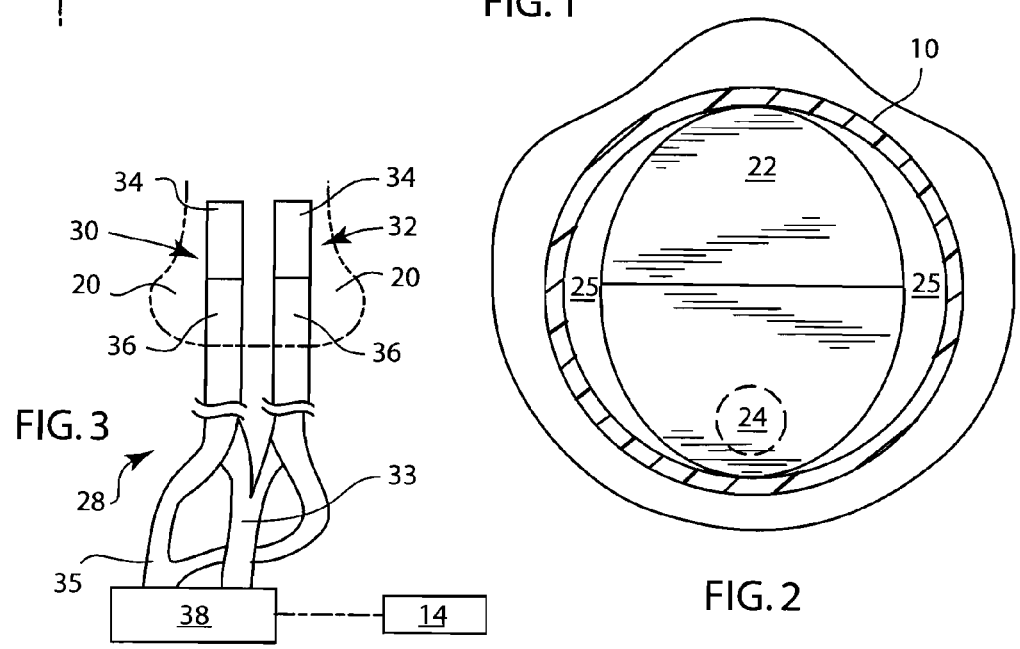
FIG. 1
FIG. 3
FIG. 2

ARRANGEMENT AND METHOD FOR DETECTING SPONTANEOUS RESPIRATORY EFFORT OF A PATIENT

FIELD OF THE INVENTION

The present invention relates to an arrangement and method for providing ventilation therapy to a patient. In general, the present invention relates to an arrangement and method for detecting patient breathing efforts such that suitable ventilatory pressure support is timely provided to the patient.

BACKGROUND AND SUMMARY

Patients that have ventilatory difficulties are often placed on a ventilator. A ventilator is a mechanical device designed to provide all or part of the work a body must produce to move gas into and out of the lungs. The ventilator delivers breathable gas to a patient and carries expired gas from the patient through a set of flexible tubes called a "patient breathing circuit".

In many instances, the patient is connected to the patient breathing circuit via a "patient/breathing circuit interface". The patient/breathing circuit interface may comprise of any one of a variety of devices that create a seal with the patient's face and/or head such that breathing gases emitted from the ventilator via the patient breathing circuit are provided to the patient's breathing passages and are not leaked to the atmosphere. The patient's "breathing passage" may include any passage that provides a link between the lungs of the patient and the patient/breathing circuit interface, such as the nasal passages, mouth, or throat. For example, many patient/breathing circuit interfaces comprise a facemask that covers the nasal passages and/or mouth of the patient. Other interfaces comprise a helmet that is worn by the patient and that creates a seal between the patient breathing circuit and the patient's head and/or face.

In certain settings, such as intensive care, a patient that is connected to a ventilator is able to breath with shallow breathes but is unable to complete a proper breathing cycle on his or her own, or in doing so requires an excessive breathing effort. In these instances, the ventilator provides only the necessary additional ventilatory support required by the patient to augment the breathing cycle. A patient's attempt to breathe "triggers" the ventilator and the ventilator then provides only the necessary pressure support to complete the inspiration. When the patient begins the expiratory phase of the breathing cycle the ventilator ceases the inspiratory pressure support and "cycles" the ventilator to provide an expiratory breath support.

Known ventilators and breathing circuits comprise a variety of flow and pressure sensors that produce signals to detect breathing efforts by the patient and to cause the ventilator to deliver a breath to the patient that is synchronous with those efforts. In known arrangements, the flow and/or pressure sensors are placed in the patient breathing circuit, in patient/breathing circuit interface, or in the ventilator. These sensors may include anemometers, ultrasonic, or differential-pressure flow sensors. These sensors are invariably-located on the ventilator side of the patient/breathing circuit interface. The sensor is applied whenever the patient is connected to the ventilator via a patient breathing circuit and a patient/breathing interface. However, with these arrangements, if the ventilator is delivering positive airway pressure and the mask is inadvertently pushed against the patient the sensing mechanism would identify the resulting flow or pressure change and interpret it as a patient's attempt to cycle the breath to expiration. This false identification would be due to the increased pressure in the facemask resulting from the inadvertent compression of the face mask. In another event, if a circuit leak occurs during the expiratory phase of the breath, the sensing mechanism would identify the resulting flow or pressure change and interpret it as a patient's attempt to trigger a breath. In the worst case scenario, the delivery of ventilatory assistance would then be in opposition to the patient's spontaneous breathing effort. Regardless, such a misinterpretation results in an asynchrony between the ventilator and the patient's respiratory efforts, ultimately reducing the assistance provided to the patient. While leaks can occur anywhere in the breathing circuit, patient/breathing circuit interface, and/or ventilator, a common location for leaks is between the patient/breathing circuit interface and the patient, which is typically where the facemask meets the patient's face, or where the helmet meets the patient's head. To mitigate such artifacts and to accommodate variations in patient breath sizes, frequently, care providers have to adjust the sensitivity of the trigger threshold to the patient activity and need. Therefore, it is desirable, in general, to provide an arrangement and method that provides early and accurate detection of patient triggers and cycle so that appropriate phase of ventilator support can be expediently delivered to the patient at the appropriate time. It is desirable, more specifically, to distinguish changes in flow and pressure that are caused by circuit leaks or compression of the breathing circuit resulting in false patient triggers and cycles, from actual patient efforts to breathe. Such an improved method or arrangement would promote synchronization between the ventilator and the patient, and ultimately provide improved ventilator support.

Another type or arrangement of sensors are used to count the number or the absence of breaths of non-intubated patients, such as used in conjunction with sleep apnea studies or apnea detection to guard against sudden infant deaths. Examples of these sensors include a thermister flow sensor or plethysmographic sensors to detect the excursion of the thorax. While these sensors are attached to the patient to monitor the occurrences of breathing, their responses tended to be slow, requiring greater than several tens or hundreds of milliseconds to measure the occurrence of a breath. It is recognized that delays in triggering mechanical ventilation assistance can cause detrimental increase in the patient work of breathing or in extreme breath dysynchrony may cause the ventilator to oppose the patient's breathing effort. The long time delay between detection of the patient's spontaneous breathing attempt and the application of mechanical ventilation assistance makes these apnea or breath detection sensors unsuitable to synchronize mechanical ventilation support of non-intubated patient.

SUMMARY OF THE INVENTION

In general, the present invention utilizes a sensor arranged to monitor flow and/or pressure changes within a breathing passage of the patient, which may include the nasal passages, mouth, throat, etc. Monitoring the changes in flow and/or pressure in the breathing passage of the patient according to the arrangements and methods described below provides accurate determination of actual patient attempts to breathe so that ventilatory support can be properly delivered to the patient at the appropriate time. The methods and arrangements of the present invention particularly distinguish between false patient triggers for the application of mechanical inspiratory breath supports. Such triggers including, but not limited to those caused by leaks in the patient breathing circuit and leaks between the patient/breathing circuit interface and the patient are distinguished from actual attempts by the patient to breathe. The methods and arrangements of the present invention also distinguish the detection of actual patient expiratory cycles over false detections that may be caused by compression of the breathing circuit. In one arrangement of the present invention, a patient/breathing circuit interface is adapted to provide a closed connection between a breathing passage of the patient and the breathing circuit. A sensing device is at least partially disposed in the breathing passage of the patient is arranged to sense a flow of gas through the breathing passage. A controller is provided that synchronizes respiratory support to the patient with actual patient attempts to breathe based upon the sensed flow of gas through the breathing passage of the patient.

The arrangement may further include a means for diverting or conditioning direct ventilator gas flow away from the sensing device or otherwise minimize confounding secondary effects of ventilator gas flows that do not contribute to gas flow into the patient breathing passages. The means may comprise a shield disposed between the facemask and the nasal passages of the patient. As gases flow into the facemask, the shield advantageously diverts and conditions the gas flow proximal to the sensor thus eliminating the potential for false readings by the sensor. Together, the sensor and shield promote improved detection of actual patient efforts to breathe. By this arrangement, attempts to breathe by the patient will result in a change in the flow of breathing gas in the patient's breathing passages, which is detected by the sensor and results in ventilatory support to the patient.

In another example, the arrangement of the present invention includes a facemask that is adapted to provide a closed connection between the nasal passages of the patient and the breathing circuit of a ventilator. According to this example, a differential pressure sensor is arranged to monitor changes in differential pressure in the nasal passages. Differences in flow or pressure caused by leaks in the patient circuit, leaks between the patient breathing circuit and the patient, typically will not result in a change of the differential pressure in the breathing passages of the patient that is indicative of a flow reversal in the patient breathing passage. As such, these occurrences will not result in an erroneous change in ventilator support.

According to one example of the method of the present invention, gas flow in the breathing passage of a patient is measured using a sensing device that is at least partially disposed in the breathing passage. Respiratory support is provided to the patient based upon the measured gas flow through the breathing passage of the patient. The sensor may comprise a differential pressure sensor. Accordingly, a change in differential pressure indicates a change in flow caused by the patient's attempt to breathe. The detection of measured differential pressure indicative of the start of flow into the nasal passage triggers inhalation support, and the detection of measured differential pressure indicative of the start of flow leaving the nasal passage cycles the ventilator to expiratory support.

However the method is not limited for use with a differential pressure sensor. In another example, a sensor measures the pressure in the patient breathing circuit or breathing circuit interface, hereafter referred as the airway pressure. Such a sensor is commonly used in conjunction with the ventilator, such as the GE Healthcare Engstrom Ventilator, and in the present invention may act as a redundant sensor to trigger spontaneous ventilation should the sensor to detect flow in the nasal passage fail or in the instance that the gas flow in the nasal passage has become completely blocked, by perhaps mucus. This sensor is in addition to the flow sensor in the patient nasal passage to detect patient inspiration and expiration phases. In this case, a measured decrease in the airway pressure, combined with a measured change of flow in the breathing passage that is towards the patient, indicates an actual attempt to inhale by the patient. If this occurs, the ventilator is triggered to provide inspiration support to the patient. A measured decrease in the airway pressure, combined with a measured change of flow in the breathing passage that is away from the patient, indicates a false trigger, such as a large leak or a disconnect in the patient breathing circuit or patient/breathing circuit interface. Such an event would not trigger ventilatory support. Correspondingly, a measured increase in the airway pressure in the breathing passage of the patient, combined with a measured change of flow that is away from the patient, indicates an actual attempt to exhale by the patient. If this occurs, the ventilator is cycled to provide expiration support to the patient. A measured increase in the airway pressure, combined with a measured change of flow that is towards the patient indicates a false trigger, such as an external compression on the patient/breathing circuit interface. Such an event would not cycle the ventilator to provide expiratory support.

These and other aspects and advantages of the present invention are described hereinbelow.

BRIEF DESCRIPTION OF THE DRAWINGS

Preferred embodiments of and the best mode of carrying out the present invention are described hereinbelow with reference to the attached drawing figures, wherein:

FIG. 1 is a side sectional view of a facemask, including a shield, worn by a patient.

FIG. 2 is a rear sectional view of the facemask taken along line 2-2 in FIG. 1.

FIG. 3 is a front sectional view taken along line 3-3 in FIG. 1.

DETAILED DESCRIPTION OF THE PREFERRED EMBODIMENTS

Figure 4:
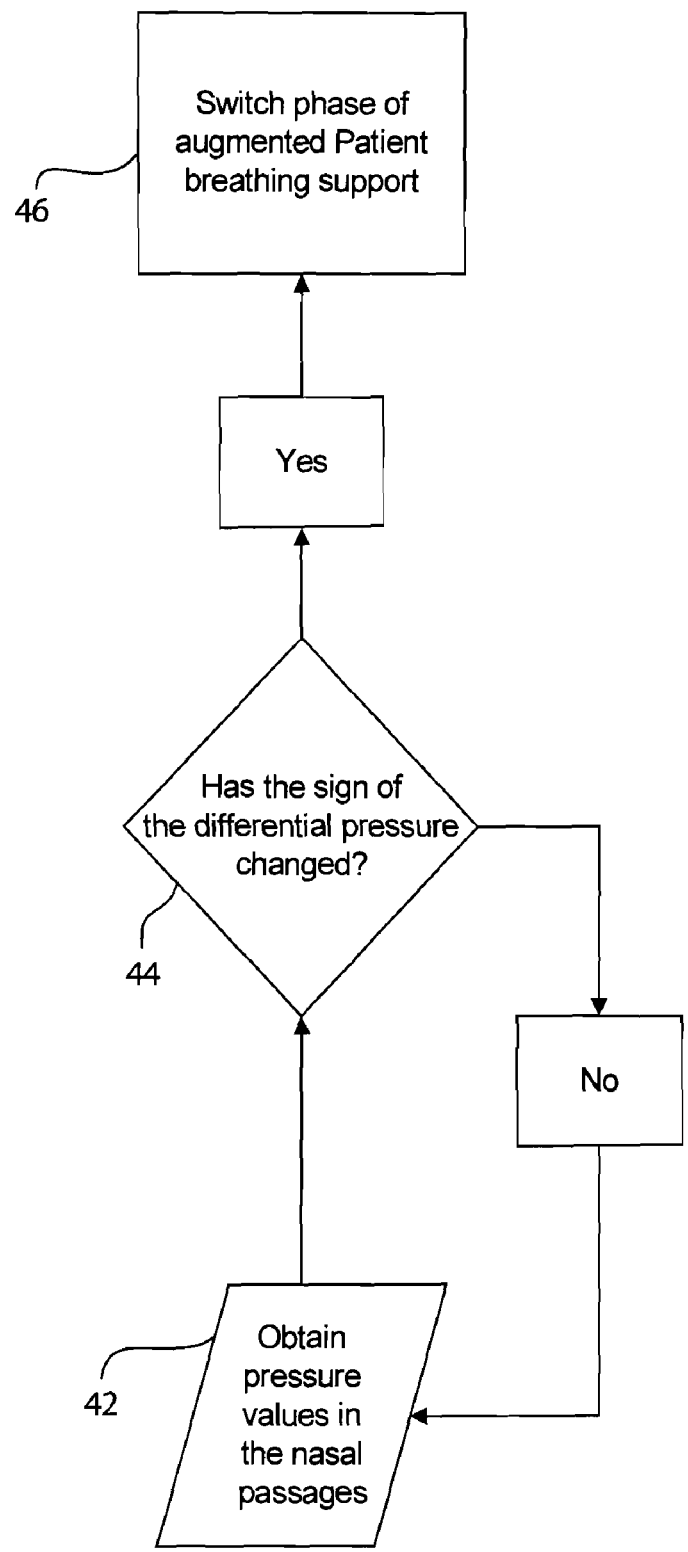
FIG. 4 is a flow-chart depicting the steps of one embodiment of the method of the present invention.

In the preferred embodiments of the present invention described in detail below, an arrangement and method for detecting spontaneous respiratory efforts of a patient is provided. It should be understood that the drawings and specification are to be considered an exemplification of the principles of the invention, which is more particularly defined in the appended claims.

Referring to FIG. 1, an arrangement for detecting actual spontaneous respiratory effort of a patient 11 receiving ventilatory support via a patient breathing circuit 12 is shown. The breathing circuit 12 is connected to the patient 11 via a patient/breathing circuit interface, which in the embodiment shown is a facemask 10, which is suitable for positive airway pressure ventilation. The facemask 10 is adapted to provide a closed connection between a breathing passage of the patient, which in FIG. 1 comprises the patient's nasal passages 20, and the breathing circuit 12. The facemask 10 and breathing circuit 12 are thus arranged to provide a flow of breathing gas from a ventilator 14 to the patient 11 according to known arrangements. The facemask 10 and breathing circuit 12 are also adapted to carry expired gases away from the patient 11 for discharge. It will be recognized by those skilled in the art that the present invention is also applicable to arrangements employing a different patient/breathing circuit interface, such as a helmet. The present invention is also applicable to arrangements delivering breathing gas to a different breathing passage of the patient.

Referring to FIG. 2, a shield 22 is positioned between the inlet 24 of the facemask 10 and the nasal passages 20 of the patient. Shield 22 may be bent as shown in FIG. 2, to conform to the facemask 10. The shield 22 is disposed within facemask 10 so that breathing gases, delivered through the breathing circuit 12, are deflected as they enter the facemask 10 so as not to directly impinge upon the flow sensor, but still allow the measurement of the gas flow as it enters the nasal passages 20 of the patient. According to the arrangement shown, the breathing gases delivered to the facemask 10 are deflected around the shield 22 and are thus delivered indirectly to the nasal passages 20 via openings 25 between the shield 22 and the facemask 10.

Referring to FIGS. 1 and 3, a sensor is disposed at least partially in the nasal passages 20 of the patient 11. In the embodiment shown, the sensor 28 comprises a differential pressure sensor 28, however it will be recognized by those skilled in the art that according to the arrangements and methods provided below, different types of pressure and/or flow sensors may be utilized to accomplish the objectives of the present invention, such as for example an anemometer.

As shown in FIGS. 1 and 3, the differential pressure sensor 28 is arranged to measure changes in the differential pressure along the nasal passages 20 of the patient 11. In the embodiment shown, the differential pressure sensor 28 includes two pairs of nasal cannulas 30, 32, one disposed in each nasal passage 20. Each pair of nasal cannulas 30, 32 comprises an upper cannula 34 and a lower cannula 36, which are offset relative to each other along the length of the nasal passage. Each upper cannula 34 and each lower cannula 36 commonly feed into respective pneumatic lines 33, 35, which lead to sensing means 38. Ideally, pneumatic lines 33 and 35 are keyed (not shown) such that they cannot be transposed when connected to the sensing means, thereby preventing errors in the detection of the breath phase. Sensing means 38 may or may not be located in the ventilator 14, but is placed in electrical communication with electronic circuitry (not shown) associated with the ventilator 14. Via the electronic circuitry, the sensing means 38 is prompted to take simultaneous pressure measurements from the respective pneumatic lines 33, 35 connected to the upper 34 and lower 36 cannulas, and then communicate the same to the ventilator 14 or to an intermediate controller or comparator.

Additionally, upon ventilator set up and initialization, a ventilator test breath that includes an inspiratory and an expiratory breath phase can be used to impose flow in and out of the nasal passage. The known flow direction of the generated test breath can be used to correlate and confirm the direction of gas flow in the nasal passage with the measured differential pressure.

The dual nasal cannula differential pressure sensor arrangement shown has been found to be particularly advantageous when used on patients that have partially blocked nasal passages. For example, if one nasal passage is blocked, the cannula disposed in the other nasal passage can still function properly.

Referring to FIG. 4, according to one embodiment of the method of the present invention, at step 42, sensing means 38 is prompted by the ventilator 14 or control mechanism to simultaneously measure the pressure in the nasal passages 20 of the patient 11 at each of the upper 34 and lower 36 cannulas. Because the upper 34 and lower 36 cannulas are disposed in the nasal passages 20 of the patient 11, actual breathing attempts by the patient 11 will cause a differential change in pressure in the cannulas 34, 36. For example the change in pressure at the upper cannula 34 may be larger than a change in pressure at the lower cannula 36, or vice versa. A reversal in the sign of the differential pressure between the upper cannula 34 and the lower cannula 36 corresponds to the reversal in the breath flow that indicates the start of an inspiration or expiration phase of the patient's breathing cycle.

Additionally, a leak in the patient breathing circuit 12, a leak between the patient 11 and the facemask 10, would not affect the sign of the differential pressure at the sensing means 38 as long as the change in the overall pressure does not cause the patient inspiration to cease, gas flow in the patient nasal passage may decrease but will continue to flow in the same direction. For example, a leak in the patient breathing circuit 12 may change the overall pressure in the nasal passages 20, however the sign of the differential pressure measured via cannulas 34, 36 would stay the same. Thus there would not be a detected measured change in the sign of the differential pressure.

At step 44, the measurements taken at the sensing means 38 are compared. As long as the differential measurements remain in the same sign, positive or negative, or substantially equal, the patient 11 has not made an actual attempt to inhale or exhale, and ventilatory support remains in the present phase of the patient's breath. The process is thereafter repeated at periodic, predetermined or selected intervals. If however, the measurements are substantially different and a sign change is detected, a change in differential pressure is realized and, at step 46, and the ventilator 14 is prompted to update the phase of the pneumatic augmentation of patient breathing.

Figure 5:
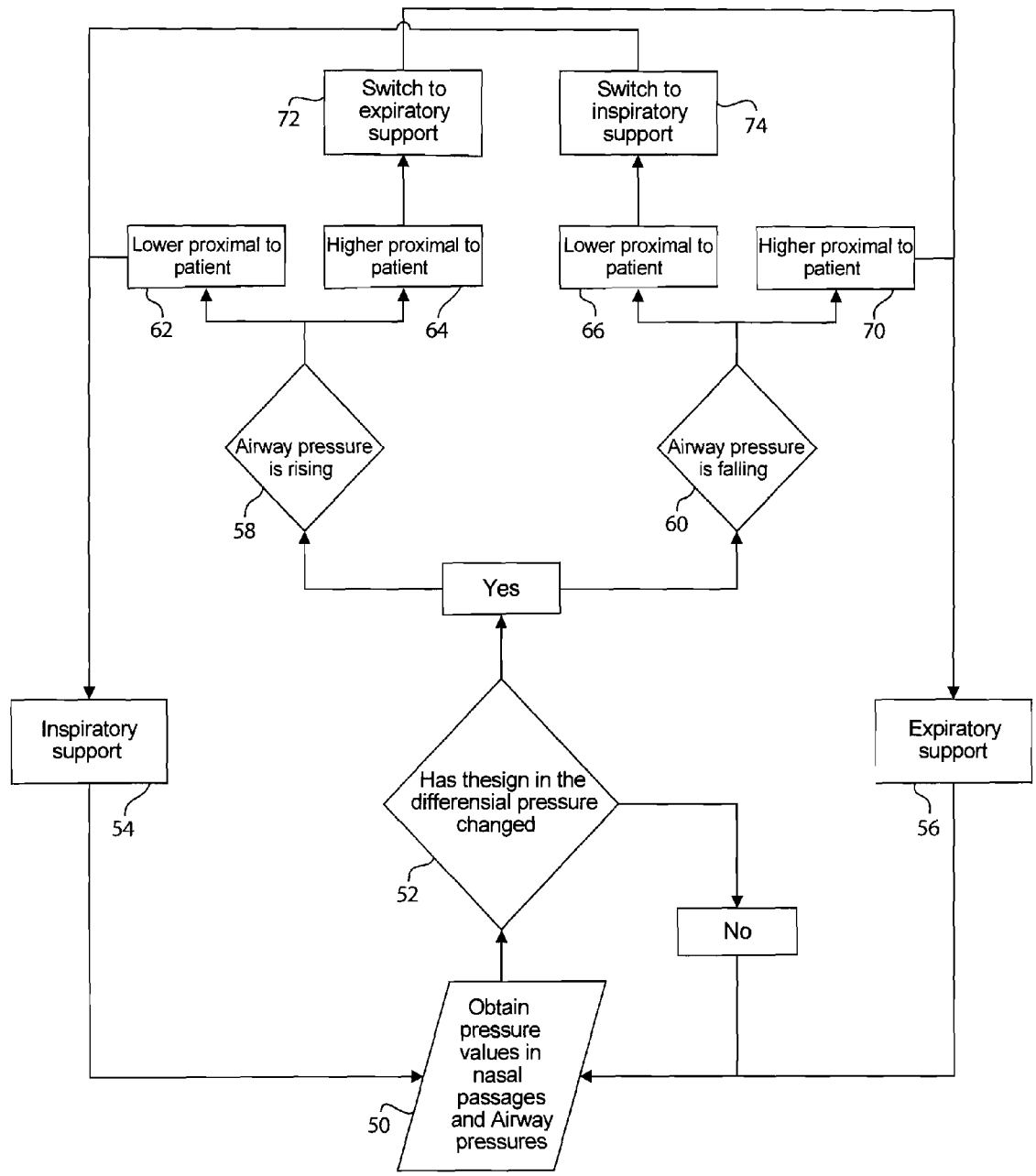
FIG. 5 is a flow-chart depicting the steps of another embodiment of the method of the present invention.

Referring now to FIG. 5, another example of the method of the present invention is depicted. According to the arrangements described above, it has been determined that one or more large leaks in the patient breathing circuit or breathing circuit interface, or large disconnects between these components can cause a rapid decrease in the airway pressure within the breathing passages of the patient resulting in the inadvertent detection of a differential pressure sign change. Also, if the patient/breathing circuit interface is compressed, for example, against the patient's face, a rapid rise in airway pressure within the breathing passages of the patient can occur and a similar inadvertent sign change detection may occur. These false patient breathing phase detection triggers negatively affect the synchronization between patient breathing attempts and ventilatory support. These disadvantages are however overcome according to the method of the present invention, one embodiment of which is depicted in FIG. 5.

Referring to FIG. 5, it is recognized by the present application that by observing and comparing the direction of change in pressure/flow in the breathing passage of the patient, and comparing this change to the change in the airway pressure, it is possible to distinguish between an actual attempt by the patient 11 to breathe and spurious disturbance to the patient/breathing circuit interface, leaks, and/or disconnects in the flow of breathing gas to the patient 11. Airway pressure is a commonly monitored ventilation parameter making decisions on the appropriate ventilator settings for the patient, ensuring appropriate ventilator delivery, and providing a means to detect adverse ventilation events.

Referring to FIG. 5, according to one embodiment of the method of the present invention, at step 50, sensing means 38 is prompted by the ventilator 14 or control mechanism to simultaneously measure the pressure in the nasal passages 20 of the patient 11 at each of the upper 34 and lower 36 cannulas, as well as the airway pressure. Because the upper 34 and lower 36 cannulas are disposed in the nasal passages 20 of the patient, actual breathing attempts by the patient 11 will cause a differential change in pressure in the cannulas 34, 36. This change can also be detected if only the upper cannula 34 is disposed in the nasal passage, and the lower cannula 36 is disposed in the breathing interface, but proximal to the nasal passage.

At step 52, the measurements taken at the sensing means 38 are compared to the data from the previous measurement. If the measurements have not changed sign, or are substantially equal, the patient 11 has not made a new attempt to inhale or exhale, and the phase of ventilatory support is not changed. The process is subsequently repeated at periodic, predetermined or selected intervals.

If, however, the measurements are substantially different and the sign has changed, it is further determined at steps 58, 60 whether the airway pressure is rising or falling. If the airway pressure is rising, at steps 62, 64, it is determined whether the differential pressure within the nasal passage 20 of the patient is higher or lower proximal to the patient, respectively. If the differential pressure proximal to the patient is lower, at step 62, the detected airway pressure change is ignored because such a change in pressure is likely due to the rising support pressure generated by the ventilator to provide inspiratory support or a compression of the patient/breathing circuit interface, or facemask 10. These events cause the airway pressure to be higher than the lung pressure give rise to the lower pressure proximal to the patient. The process is then repeated at periodic, predetermined, or selected intervals. If, at step 64, the differential pressure is higher proximal to the patient, and the ventilator is cycled to provide expiration support to the patient 11. This condition is consistent with the patient attempt to expire gases by spontaneously increasing the pressure in the patient lungs above the airway pressure (accounting for the higher differential pressures proximal to the patient), and pushing gases into the patient breathing circuit (accounting for the rising airway pressure).

Alternatively, if the airway pressure is falling, at step 60, it is further determined whether the pressure proximal to the patient is lower at step 66, or higher at step 70. If the pressure proximal to the patient is higher, at step 70, the event is ignored because it is likely due to decreasing support pressure generated by the ventilator to provide expiratory support, or a large leak or disconnection in the patient/breathing circuit interface or patient breathing circuit. The ventilation support mode remains in its current phase of expiratory support. The process is then repeated at periodic, predetermined, or selected intervals. If the pressure proximal to the patient is lower, at step 66, the ventilator is triggered to provide inspiration support to the patient. This condition is consistent with the patient attempt to inspire gases by spontaneously decreasing the pressure in the patient lungs below the airway pressure (accounting for the lower differential pressures proximal to the patient), and drawing gases away from the patient breathing circuit (accounting for the falling airway pressure).

It is further recognized that the inflow of breathing gases from the patient breathing circuit 10 either directed at the flow sensor can undesirably cause secondary measurement artifact to the differential pressure measurement in the nasal passages 20. By the present invention it is realized that such artifact to the differential pressure measurement in the nasal passages 20 can be eliminated by diverting the flow of breathing gases such that it does not flow directly at the differential flow sensor. In the particular embodiment shown, means for diverting the flow of breathing gases comprise the shield 22.

Furthermore, if cannula 36, shown in FIG. 3, is disposed in the breathing circuit interface, ventilator bias gas flows that impinges directly on the opening of cannulas 36 but do not enter the patient breathing passages can cause artifacts in the differential pressure measurement. In this case, the choice of a small orifice to cannula 36 can minimize or eliminate these flow induced differential pressure measurement artifacts.

By the present arrangement and method it is therefore possible to accurately identify patient attempts to breathe and provide efficient ventilator support to the patient 11. The described arrangement and method overcomes current detection systems which cannot accurately determine whether changes in pressure in the breathing circuit represent an actual attempt to breathe, or rather whether the changes in pressure are the result of a leak or other inadvertent ventilatory delivery event. The present arrangement and method provides early and accurate detection of patient attempts to breathe such that pressure support can be expediently delivered to the patient at the necessary time. The present arrangement and method further allows for synchronization between the ventilator and the patient and ultimately provides improved ventilator support.

While this invention is susceptible to embodiments in many different forms, the drawings and specification describe in detail a preferred embodiment of the invention. They are not intended to limit the broad aspects of the invention to the embodiment illustrated.

What is claimed is:

1. A method for detecting spontaneous respiratory effort of a patient connected to a patient/breathing circuit interface and receiving ventilatory support, the method comprising the steps of:
   placing a pressure sensor at least partially into a breathing passage of the patient, wherein the pressure sensor is disposed between the interface and the patient; and
   monitoring changes in the airway pressure;
   monitoring a direction of change of differential pressure along the breathing passage of the patient; and
   comparing the changes in airway pressure and the direction of the change in differential pressure to detect a spontaneous patient respiratory effort.

2. The method of claim 1, wherein monitoring the change in airway pressure comprises the step of comparing a differential pressure measurement to a previous differential pressure measurement to determine if the pressure is rising or falling within the patient's breathing passage.

3. The method of claim 1, wherein the breathing passage is a nasal passage of the patient.

4. The method of claim 1, wherein the pressure sensor comprises upper and lower cannulas that are offset relative to each other, wherein the upper cannula is placed deeper into the breathing passage of the patient than the first cannula.

5. The method of claim 4, wherein the step of monitoring the direction of change of the differential pressure along the breathing passage of the patient comprises the steps of:
   (a) calculating the differential between first and second pressures taken from the upper nasal cannula at one moment in time;
   (b) calculating the differential between first and second pressures taken from the lower nasal cannula at the one moment in time;
   (c) calculating the differential between the differentials obtained in steps (a) and (b);
   (d) calculating the differential between third and fourth pressures taken from the upper nasal cannula a subsequent moment in time;

(e) calculating the differential between third and fourth pressures taken from the lower nasal cannula at the subsequent moment in time;

(f) calculating differential between the differentials obtained in steps (d) and (e); and (g) comparing the differential obtained in step (c) to the differential obtained in step (f) to determine the direction of change of the differential pressure along the breathing passage of the patient.

6. The method of claim 1, comprising the step of providing expiratory support to the patient if the airway pressure is rising and the direction of change in differential pressure is higher proximal to the patient.

7. The method of claim 1, comprising the step of maintaining a current phase of respiratory support to the patient if the airway pressure is rising and the direction of change in differential pressure is lower proximal to the patient.

8. The method of claim 1, comprising the step of maintaining a current phase of respiratory support to the patient if the airway pressure is falling and the direction of change in differential pressure is higher proximal to the patient.

9. The method of claim 1, comprising the step of providing inspiratory support to the patient if the airway pressure is falling and the differential pressure is lower proximal to the patient.

10. An arrangement for detecting spontaneous respiratory effort of a patient receiving ventilatory support via a patient breathing circuit, the arrangement comprising:

a patient/breathing circuit interface, the interface being configured to provide a closed connection between a breathing passage of the patient and the breathing circuit;

a sensing device, the sensing device comprising a differential pressure sensor configured to be at least partially disposed in the breathing passage of the patient and to sense a flow of gas through the breathing passage and changes in airway pressure; and a controller, the controller configured to compare changes in airway pressure and a direction of change in differential pressure along the breathing passage to detect a spontaneous patient respiratory effort.

11. The arrangement of claim 10, wherein the controller is configured to monitor the change in airway pressure by comparing a differential pressure measurement to a previous differential pressure measurement to determine if the pressure is rising or falling within the patient's breathing passage.

12. The arrangement of claim 10, wherein the breathing passage is a nasal passage of the patient.

13. The arrangement of claim 10, wherein the pressure sensor comprises upper and lower cannnulas that are offset relative to each other, wherein the upper cannula is configured to be placed deeper into the breathing passage of the patient than the first cannula.

14. The arrangement of claim 13, wherein the controller is configured to monitor the direction of change of the differential pressure along the breathing passage of the patient by:

(a) calculating the differential between first and second pressures taken from the upper nasal cannula at one moment in time;

(b) calculating the differential between first and second pressures taken from the lower nasal cannula at the one moment in time;

(c) calculating the differential between the differentials obtained in steps (a) and (b);

(d) calculating the differential between third and forth pressures taken from the upper nasal cannula a subsequent moment in time;

(e) calculating the differential between third and forth pressures taken from the lower nasal cannula at the subsequent moment in time;

(f) calculating differential between the differentials obtained in steps (d) and (e); and (g) comparing the differential calculated in step (c) to the differential obtained in step (f) to determine the direction of change of the differential pressure along the breathing passage of the patient.

15. The arrangement of claim 10, wherein the controller is configured to control a ventilator to provide expiratory support to the patient if the airway pressure is rising and the direction of change in differential pressure is higher proximal to the patient.

16. The arrangement of claim 10, wherein the controller is configured to control a ventilator to maintain a current phase of respiratory support to the patient if the airway pressure is rising and the direction of change in differential pressure is lower proximal to the patient.

17. The arrangement of claim 10, wherein the controller is configured to control a ventilator to maintain a current phase of respiratory support to the patient if the airway pressure is falling and the direction of change in differential pressure is higher proximal to the patient.

18. The arrangement of claim 10, wherein the controller is configured to control a ventilator to provide inspiratory support to the patient if the airway pressure is falling and the differential pressure is lower proximal to the patient.

* * * * *